United States Patent
Chen et al.

(10) Patent No.: US 11,623,085 B2
(45) Date of Patent: Apr. 11, 2023

(54) DEVICES AND METHODS FOR TREATMENT OF TUMORS USING ELECTROMAGNETIC SIGNAL

(71) Applicant: Regents of the University of Minnesota, Minneapolis, MN (US)

(72) Inventors: Clark C. Chen, Edina, MN (US); Gregory Frederick Molnar, Blaine, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/250,735

(22) PCT Filed: Aug. 29, 2019

(86) PCT No.: PCT/US2019/048858
§ 371 (c)(1),
(2) Date: Feb. 26, 2021

(87) PCT Pub. No.: WO2020/047285
PCT Pub. Date: Mar. 5, 2020

(65) Prior Publication Data
US 2021/0346692 A1    Nov. 11, 2021

Related U.S. Application Data

(60) Provisional application No. 62/724,177, filed on Aug. 29, 2018.

(51) Int. Cl.
*A61N 1/05*     (2006.01)
*A61N 1/36*     (2006.01)
(Continued)

(52) U.S. Cl.
CPC ....... *A61N 1/36002* (2017.08); *A61N 1/0534* (2013.01); *A61N 1/36171* (2013.01);
(Continued)

(58) Field of Classification Search
CPC .... A61N 1/40; A61N 1/36002; A61N 1/0534; A61N 1/36171; A61N 1/37211;
(Continued)

(56) References Cited

U.S. PATENT DOCUMENTS 6,366,808 B1    4/2002    Schroeppel et al.
6,901,296 B1    5/2005    Whitehurst et al.
(Continued)

FOREIGN PATENT DOCUMENTS

CN     202982928 U    6/2013
WO     WO2009044289 A1    4/2009
(Continued)

OTHER PUBLICATIONS

International Preliminary Report on Patentability, International Application No. PCT/US2019/048858, dated Mar. 11, 2021, 9 pages.
(Continued)

*Primary Examiner* — Carl H Layno
*Assistant Examiner* — Anh-Khoa N Dinh
(74) *Attorney, Agent, or Firm* — Merchant & Gould P.C.

(57) ABSTRACT

Systems and methods for treating cancerous tumors (including glioblastoma multiforme (GBM)) with electrotherapy, such as deep brain stimulation (DBS) technology, as disclosed herein. One or more configurations can be generated based on a patients tumor characteristics. The selected configurations can be electrode configurations or settings for an electrical source coupled to the electrodes. The one or more configurations can be targeted for inhibiting cell growth process, such as to inhibit mitosis, immune suppression, or to inhibit DNA replication. Inhibition of cell growth processes can initiate death of the cancerous cells.

19 Claims, 11 Drawing Sheets

(51) Int. Cl.
  *A61N 1/372* (2006.01)
  *A61N 1/40* (2006.01)
  *B33Y 80/00* (2015.01)

(52) U.S. Cl.
  CPC ............ *A61N 1/37211* (2013.01); *A61N 1/40* (2013.01); *B33Y 80/00* (2014.12)

(58) Field of Classification Search
  CPC ...... A61N 1/05; B33Y 80/00; A61B 18/1206; A61B 18/14; A61B 2018/00321; A61B 2018/00482; A61B 2018/00565; A61B 2018/00577; A61B 5/0042; A61B 5/4064; A61B 5/6868; A61B 5/4848; A61B 2576/026; G16H 30/40
  See application file for complete search history.

(56) References Cited

U.S. PATENT DOCUMENTS

| | | | |
|---|---|---|---|
| 7,395,112 | B2 | 7/2008 | Keisari et al. |
| 8,406,870 | B2 | 3/2013 | Palti |
| 9,037,227 | B2 | 5/2015 | Slizynski et al. |
| 9,155,889 | B2 | 10/2015 | Hershey |
| 2002/0198567 | A1 | 12/2002 | Keisari et al. |
| 2004/0010290 | A1* | 1/2004 | Schroeppel ........ A61N 1/36002 607/3 |
| 2004/0176804 | A1* | 9/2004 | Palti ........................ A61N 1/326 607/2 |
| 2005/0222623 | A1 | 10/2005 | Kroll et al. |
| 2007/0225766 | A1 | 9/2007 | Palti |
| 2017/0120041 | A1* | 5/2017 | Wenger .................... A61N 1/32 |
| 2017/0281934 | A1 | 10/2017 | Giladi et al. |
| 2017/0312388 | A1 | 11/2017 | Shoseyov et al. |

FOREIGN PATENT DOCUMENTS

| | | |
|---|---|---|
| WO | WO 2014/181167 A1 | 11/2014 |
| WO | WO 2016/179712 A1 | 11/2016 |
| WO | WO-2016179712 A1 * | 11/2016 ............ A61K 41/00 |
| WO | WO 2018/057953 A2 | 3/2018 |

OTHER PUBLICATIONS

International Search Report, International Application No. PCT/US2019/048858, dated Jan. 2, 2020, 12 pages.

Stupp et al., "NovoTTF-100A versus physician's choice chemotherapy in recurrent glioblastoma: a randomised phase III trial of a novel treatment modality." Eur J Cancer. Sep. 2012;48(14):2192-202. doi: 10.1016/j.ejca.2012.04.011. Epub May 18, 2012.

Lok et al., "Analysis of physical characteristics of Tumor Treating Fields for human glioblastoma." Cancer Med. Jun. 2017;6(6): 1286-1300. doi: 10.1002/cam4.1095. Epub May 23, 2017.

Korshoej Ar "Impact of tumor position, conductivity distribution and tissue homogeneity on the distribution of tumor treating fields in a human brain: A computer modeling study." PLoS One. Jun. 12, 2017;12(6):e0179214. doi: 10.1371/journal.pone.0179214. eCollection 2017.

Kirson Ed "Alternating electric fields arrest cell proliferation in animal tumor models and human brain tumors." Proc Natl Acad Sci USA. Jun. 12, 2007; 104(24):10152-7. Epub Jun. 5, 2007.

Shen Y, "Orthogonal targeting of EGFRvIII expressing glioblastomas through simultaneous EGFR and PLK1 inhibition." Oncotarget. May 20, 2015;6(14):11751-67.

Stupp, "Maintenance Therapy With Tumor-Treating Fields Plus Temozolomide vs Temozolomide Alone for Glioblastoma: A Randomized Clinical Trial." JAMA. Dec. 15, 2015;314(23):2535-43. doi: 10.1001/jama.2015.16669.

Miocinovic S, "History, applications, and mechanisms of deep brain stimulation." JAMA Neurol. Feb. 2013;70(2):163-71. doi: 10.1001/2013.jamaneurol.45.

Zhu P, "Tumor treating fields: a novel and effective therapy for glioblastoma: mechanism, efficacy, safety and future perspectives." Chin Clin Oncol. Aug. 2017;6(4):41. doi: 10.21037/cco.2017.06.29.

Wenger C, "Modeling Tumor Treating fields (TTFields) application within a realistic human head model." Conf Proc IEEE Eng Med Biol Soc. 2015;2015:2555-8. doi: 10.1109/EMBC.2015.7318913.

* cited by examiner

DEVICES AND METHODS FOR TREATMENT OF TUMORS USING ELECTROMAGNETIC SIGNAL

PRIORITY CLAIM

The present application is a National Phase entry of PCT Application No. PCT/US2019/048858, filed Aug. 29, 2019, which claims priority from U.S. Provisional Application No. 62/724,177, filed Aug. 29, 2018, each of which is hereby fully incorporated herein by reference.

TECHNICAL FIELD

Embodiments relate to devices and methods for the treatment of cancerous or other tissues having different response to electrical stimuli based upon their physical properties as compared to surrounding, healthy or non-cancerous tissues.

BACKGROUND

Current cancer treatments rely on compounds and methodologies that are generally toxic or damaging to human tissues and cells. These treatments are often equally, if not more, dangerous to healthy tissue and cells than they are to the cancer. Evidence that tumor cells fail to thrive under the effects of an electric field allows for the development of treatment which will preferentially attack tumor cells, leaving healthy tissue unaffected. The brain, and more generally the central nervous system, is ideal for such a treatment, due to the pronounced difference between the characteristics of a Central Nervous System (CNS) neuron and those of a tumor cell. In particular, the static nature of a mature neuron protects the healthy cells from many effects to which the rapidly dividing tumor cells are vulnerable.

Glioblastoma multiforme (GBM) is a highly aggressive brain tumor. The prognosis of a patient with GBM is extremely poor, with nearly uniform fatality within two years of diagnosis. GBM is the most common form of brain cancer, affecting both men and women of any age. The incidence rate of GBM tumors is approximately 3 in 100,000 per year in the United States, or about 10,000 new cases each year. There are about 64,000 new tumors of the central nervous system and 17,000 primary brain tumors diagnosed in the United States each year.

Efforts to improve the prognosis of GBM patients have had little success. Standard treatment for GBM includes surgical resection, whenever possible. Such treatment is difficult because GBM tumors are generally invasive and located in areas of the brain that control the senses, motor function, and speech. Surgical resection is then followed by radiotherapy and chemotherapy. These treatments are harmful to healthy brain tissue adjacent to the treated area, which further limits the efficacy of treatment via radiotherapy.

Further, these techniques are not curative due to the invasiveness of the tumor. GBM tumors are often associated with the migration of malignant cells to adjacent, otherwise healthy areas of the brain. This often results in a primary tumor surrounded by multiple microscopic tumors that cannot be imaged to permit surgical resection and thus cannot be easily detected for removal. The effectiveness of radiation and chemotherapy are significantly hindered by the unique anatomy of the central nervous system. Even with such treatment, the median survival time for GBM patients is about one year or less, and less than 2% of patients survive three years. This also further complicates the already difficult task of maintaining the effectiveness of chemotherapy in the face of cancer's rapid adaptability.

Recent efforts have suggested that external electrode therapy can improve the prognosis of GBM patients. The malignancy of cancer is attributable to uncontrolled cell proliferation, which is largely mediated by interactions between highly charged molecules. Recently, application of electric fields to the scalp has been used disrupt interactions among charged molecules, which reduces cancer proliferation.

However, these efforts have demonstrated limited efficacy due to the restrictions imposed by applying electrodes to the skin. By directing the electric fields a distance through the skull and soft tissue, the strength of the field applied to the cancerous cells is dampened. A need exists, therefore, to optimize the strength and specificity of the field that is applied to the cancerous cells. This need applies not only to GBM but to all tumor types where adjacent, healthy tissue could be damaged by conventional treatments.

SUMMARY

The present disclosure provides advantages over existing standard of care treatments for cancer by providing the effectiveness of a multi-drug regimen without the toxicity associated with pharmaceutical treatments. Additionally, implantation of the leads is minimally invasive, providing advantages over surgical resection. Thus, the present disclosure provides for a cancer treatment both more effective and with less damaging collateral effects than existing treatments.

Embodiments of the present disclosure include DBS systems and methods for delivering electric fields directly to a tumor for treatment of various cancers, such as GBM. The disclosed systems and methods produce a range of stimulation settings that can impede or stop cell growth for a plurality of tumor types. In embodiments, target objectives can include mitosis inhibition, immune suppression, and inhibition of DNA replication processes, all of which can halt growth of cancerous cells. Embodiments may act as an electromagnetic (EM) analog to a multi-drug, and combine target objectives in parallel, sequence, or a cycle to meet the rapid adaption of cancer cells to a particular mode of inhibition.

A method for programming a signal generator with a DBS lead configured to deliver stimulation to a tumor is disclosed. The method can comprise generating a tumor profile based on one or more characteristics of the tumor, generating one or more electrode configurations and one or more sets of stimulation settings based on the tumor profile, and providing, to a signal generator, the selected sets of stimulation settings.

The tumor profile can be acquired by using an imaging modality to capture the tumor and then generating a tumor profile based on the imaging data. The profile can then be used to select electrode configurations to create a desired Volume of Tissue Activation (VTA), which can be customizable to each patient's unique tumor. The stimulation delivered by the selected electrodes can be applied based on a set of stimulation settings. Electrode configurations and stimulation settings can be selected by a computer algorithm based on the desired effect on the tumor. Various sets of stimulation settings can be used in order to provide optimal treatment to the patient. Sets of stimulation settings can be selected based on the specific cell process that is targeted. For example, stimulation settings may be selected to target inhibition of mitosis, immune suppression, or inhibition of DNA replication. Computer algorithms can be used to select the electrode configuration and stimulation settings for each individual patient. Furthermore, various sets of stimulation settings may be delivered simultaneously, cyclically, asynchronously/independently, or in an alternating fashion.

A system comprising an algorithm according to which one or more tumor characteristics are utilized to select stimulation settings intended to disrupt tumor cell growth processes is disclosed. The system comprises a signal generator coupled to one or more leads configured to be implanted such that the generated electric field is applied directly within a tumor. The leads comprise one or more electrodes, which are configured to produce an optimal electric field/VTA based on the desired effect on the tumor. The system further comprises a programmer in communication with the signal generator and configured to deliver stimulation to the electrodes according to the selected stimulation parameters.

The system can select the desired electrode configuration from a set of readily available leads, or it can design custom electrode configurations based on the desired effects on the tumor. The system also can apply various sets of stimulation settings to the tumor via the electrode configuration. When more than one set of settings is selected, the system can apply the sets of settings simultaneously, cyclically, asynchronously/independently, or in an alternating fashion. The system can also select stimulation settings based on the specific cell process that is targeted. For example, the system may select stimulation parameters to target mitosis, immune suppression, prevention of inflammation, or inhibition of DNA replication, among others.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
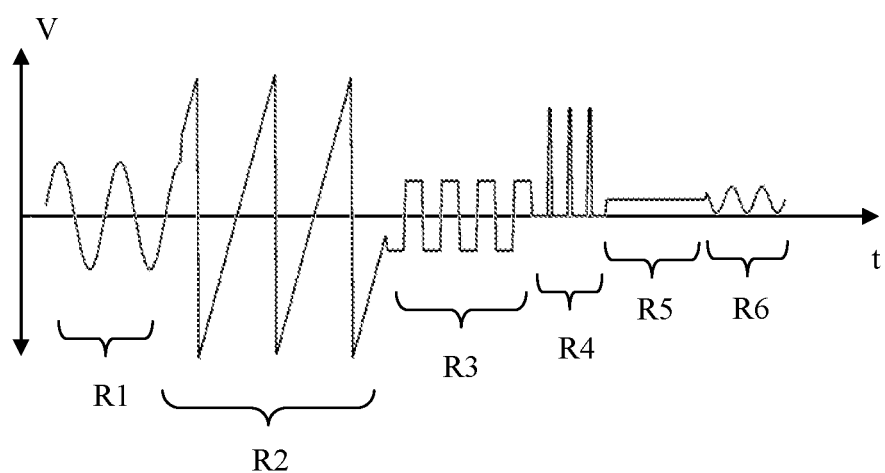
FIG. 1 is an example waveform that can be used for treatment of a tumor, according to an embodiment.

Various features and elements discussed herein are not necessarily drawn to scale, with some elements being enlarged in the drawings for the purposes of illustration and to aid understanding. While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Various embodiments described herein relate to treatment of cancers, including GBM, with electromagnetic therapy. The therapies described herein do not require the administration of a pharmaceutical drug (though in some cases a medical practitioner may use these therapies in conjunction with pharmaceuticals), while still providing the benefits of a multi-drug regimen.

I. Definitions

Various terms are used throughout this application that have specific definitions or are used in specific ways within the instant application. Among these are:

Minimally Invasive: surgery or other treatment designed to limit trauma to the body of the patient, in particular to limit the size of incisions needed, minimizing the patient's pain, healing time, and subsequent risk of infection.

Non-Specific Electric Field: an electric field having a size and shape based upon a tumor's 3-dimensional profile and type, which may spread beyond the tumor to include a surrounding area of healthy tissue.

Tumor Data: information regarding a tumor that is being treated, which can include (but is not limited to) one or more of tumor shape, location, density, size, or volume.

Electrical parameters: those parameters that can be used to set the operation of electrodes described herein, which can include (but is not limited to) amplitude, pulse width, frequency, waveform or pulse shape, pulse pattern, field orientation, or burst parameters.

Computing and other devices are discussed herein that can include memory. Memory can comprise volatile or non-volatile memory as required by the coupled computing device or processor to not only provide space to execute the instructions or algorithms, but to provide the space to store the instructions themselves. In one embodiment, volatile memory can include random access memory (RAM), dynamic random access memory (DRAM), or static random access memory (SRAM), for example. In one embodiment, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In one embodiment, the system or components thereof can comprise or include various modules or engines, each of which is constructed, programmed, configured, or otherwise adapted to autonomously carry out a function or set of functions. The term "engine" or "module" as used herein is defined as a real-world device, component, or arrangement of components implemented using hardware, such as by an application specific integrated circuit (ASIC) or field-10 programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

II. Electrical Field as Targeted Drug Substitute

As described above, the application of electromagnetic radiation, or the application of alternating current, are used in embodiments described herein to provide an analog to a multi-drug treatment. In a conventional multi-drug treatment, a patient is given a drug that can reduce or eliminate a tumor. The tumor is monitored and, so long as the drug is still effective, the treatment remains substantially unchanged. Once the treatment begins to lose efficacy, however, a medical professional may modify the drug or add some additional drug that operates in a different way.

Similarly, the embodiments described herein provide electromagnetic treatment to destroy or reduce a tumor, and the various electrical parameters used in the treatments are analogous to the various drugs that have been used conventionally. One type of electrical parameter input may result in destruction of a tumor for a time, only to begin losing efficacy later. The electrical parameters can be changed throughout treatment in a similar fashion to pharmaceutical changes, with several key distinctions.

First, unlike a multi-drug treatment, the embodiments described herein can be targeted to a precise area and the treatment itself can be modified nearly instantaneously. Pharmaceuticals are typically delivered venously or orally, and in either case are delivered throughout the body, which can have various adverse effects. Pharmaceuticals can also create adverse interactions with other medications, and it may not be possible to administer a desired treatment plan without changing other medications or schedules. Furthermore, pharmaceuticals require relatively long time periods to take effect and, importantly, also require significant time periods to wear off and leave the patient's system, leaving no option for rapid response to changes in the tumors behavior by adjusting the pharmaceutical regimen. Though methodologies exist to target pharmaceutical treatments to particular cells, they often require additional steps in the treatment and pose the same systemic risks to the patient as the pharmaceuticals themselves.

For all these reasons, the conventional, pharmaceutical approach to tumor reduction is not ideal. Although medical practitioners recognize the benefit of rapidly changing treatment for cancers, none have previously proposed the solution described herein, which provides localized and rapidly changeable electromagnetic treatment to a tumor.

FIG. 1 is a graph of voltage over time for a hypothetical treatment plan. FIG. 1 includes six separate treatment regions (R1-R6), each of which corresponds to a different set of electrical parameters. R1 is a treatment region in which a sine wave signal is provided, R2 is a treatment region corresponding to a sawtooth wave, R3 is a treatment region corresponding to a square wave, R4 is a treatment region corresponding to a series of pulses, R5 is a treatment region corresponding to a constant voltage, and R6 is a treatment region that corresponds to a combination of both a constant voltage and a sine wave. Notably, in each region the electrical parameters in addition to wave shape vary, such as frequency and amplitude. Adjusting these parameters can have various effects on the cells of the patients bode and the cancer. For example, increases in voltage and pulse width are known to alter membrane potentials and increase the permeability of cells.

III. Deep Brain Stimulators Case Study

DBS has been approved by the Food and Drug Administration (FDA) for treatment of neuro-degenerative diseases, such as Parkinson's disease. Furthermore, the safety of implantation of electrodes, even long-term, for DBS is well established. This being said, electrode design and electric fields required to disrupt cancer cell growth diverge significantly from those used to treat neuro-degenerative diseases. The need exists, therefore, for a DBS device that utilizes an electrode configuration and electric field configured specifically for the disruption of the various processes of cell proliferation for treatment of GBM. According to embodiments, an electric field can be applied directly to a tumor for disruption of one or more tumor proliferation processes.

Table 1 depicts example frequency ranges that target specific tumor or cellular processes. Electric fields with these or other frequency ranges can be delivered simultaneously, in an alternating fashion, or in a cyclical manner in order to optimally disrupt the tumor cell proliferation processes.

TABLE 1

| Frequency Range (Hz) | Effect |
| --- | --- |
| 61-200 | Inhibit cellular mitosis |
| 300-700 | Initiate immune suppression |
| 1,000+ | Inhibit DNA processes |

The examples in Table 1 are only some of the possible frequency ranges and effects, and others can be implemented in other to disrupt, inhibit or otherwise affect one or more particular or desired tumor cellular processes. For example, multiple frequencies can be delivered simultaneously to disrupt multiple processes all at once, or in a predefined pattern or in response to biological data. These frequencies also can be tuned to the patient's tumor characteristic or response behavior. In addition to modulating the intracellular processes within cancer cells, the electric field can modulate the content of the tumor microenvironment, including recruitment of immune cells.

Electromagnetic fields may interfere with various cellular processes, depending on widely variable features of the field. For example, clear indicators and mechanisms have been identified to show disruption of mitotic spindle formation by low frequency (e.g., <500 Hz) fields. Such low frequency fields interfere with the arrangement and stability of microtubules, the tubular cytoskeletal polymers that form the mitotic spindle. Chemical anti-microtubule agents already see widespread clinical use against multiple cancer types; however they carry the same risks of damage to healthy tissue. The spindle is necessarily a dynamic structure, due to its function of capturing and segregating chromosomes between daughter cells, and microtubules are inherently polar, resulting in mitotic spindles having distributed dipoles throughout their structure. Disrupting the arrangement of the microtubules causes the spindles to become increasingly fragile, resulting in the accumulation of mitotic defects in the progeny cells and/or cell cycle arrest of the parent at M phase. In many eukaryotic cells, even a relatively short delay in M phase may cause the cell to cease cycling and ultimately trigger an apoptosis pathway. The aneuploidy and polyploidy characteristics accumulated through the cell line also lead to apoptosis through various pathways, especially if continual prevention of proper spindle formation allows chromosomal errors to accumulate at a rate which prevents stabilization of the cell line by the cancer's altered tumor suppressor activity.

Additionally, altering voltage and pulse width are known to alter membrane potential and increase cell permeability. Other parameters alter the characteristics of the field in other helpful ways, for instance the amplitude of a particular signal factors into the size of the field generated.

Figure 2A:
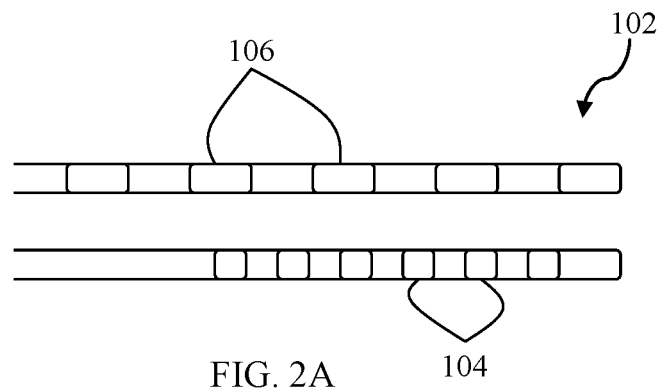
FIG. 2A is a simplified schematic of an electrode pair, according to an embodiment.

Referring now to FIG. 2A, an example lead 102 is depicted. Lead 102 is configured with input regions 104 and output regions 106. Lead 102 is configured with 1:1 internal connection of the distinct input and output channels. That is, the lead electrodes and the stimulator can be constructed and connected to allow for multiple independent control. In this way, each electrode can be independently configured to serve as an anode or a cathode, and each electrode could also deliver an independent set of treatment parameters. Each of the electrodes can deliver their specific stimulation therapy, independently, simultaneously, or in interleaved patterns with respect to the other electrodes.

Figure 2B:
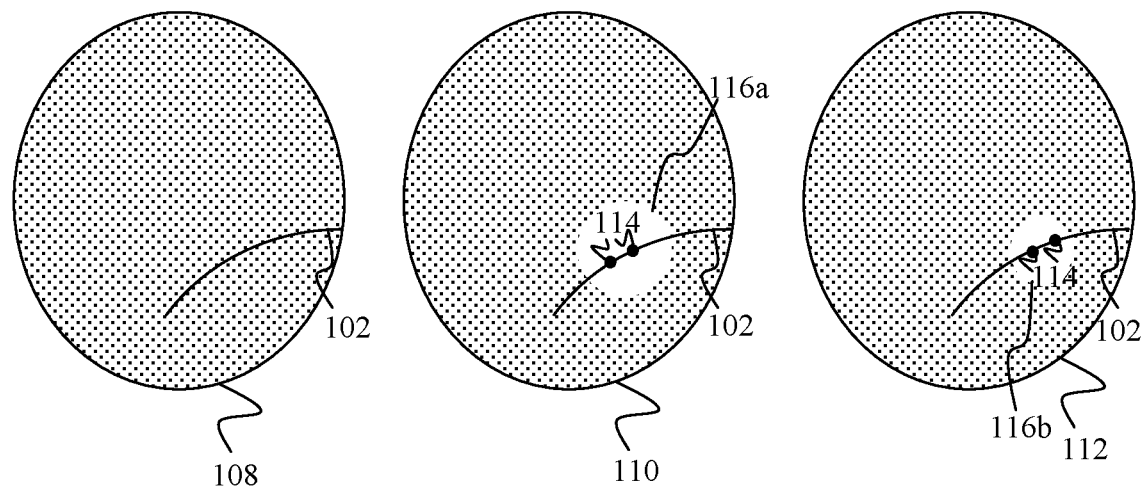
FIG. 2B depicts test data corresponding to treatment of a tumor by an embodiment.

FIG. 2B depicts lead 102 in use in an in vitro environment. Plates 108, 110, and 112 each depict a 10 cm cell culture dish with crystal violet staining of tumor cells after a specific duration of electric field application via lead 102 (24 hours in this example, though the duration can be different for other treatments). Crystal violet staining was performed thereafter. Control plate 108 was fitted with an electrode without an active electric field, with active electrode portions 114. Test plates 110 and 112 show the results of an active electrode delivering waveforms at 100 Hz (plate 110) and 200 kHz (plate 112). Cleared zones 116a and 116b demonstrate tumor cell death in the vicinity of active electrode portions 114.

Figure 2C:
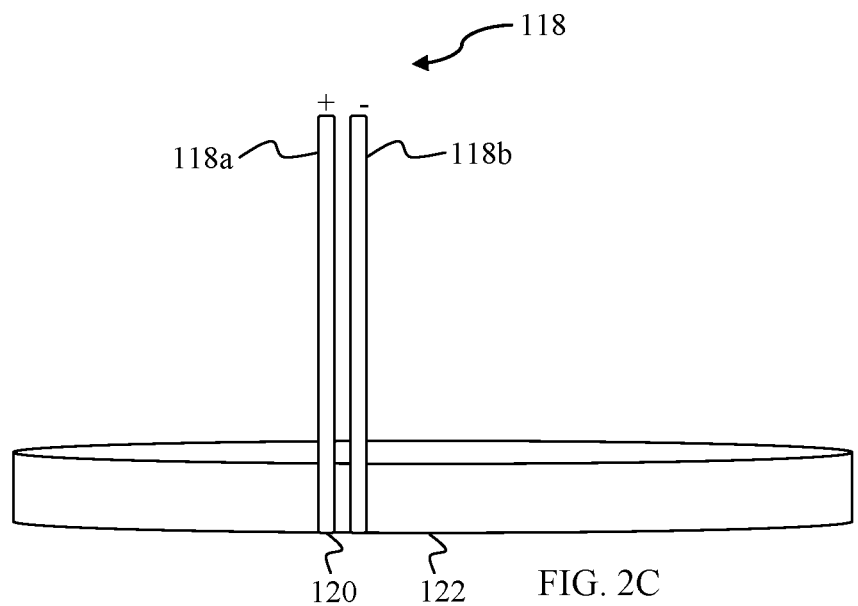
FIG. 2C is a side view of an electrode pair according to an embodiment.
Figure 2D:
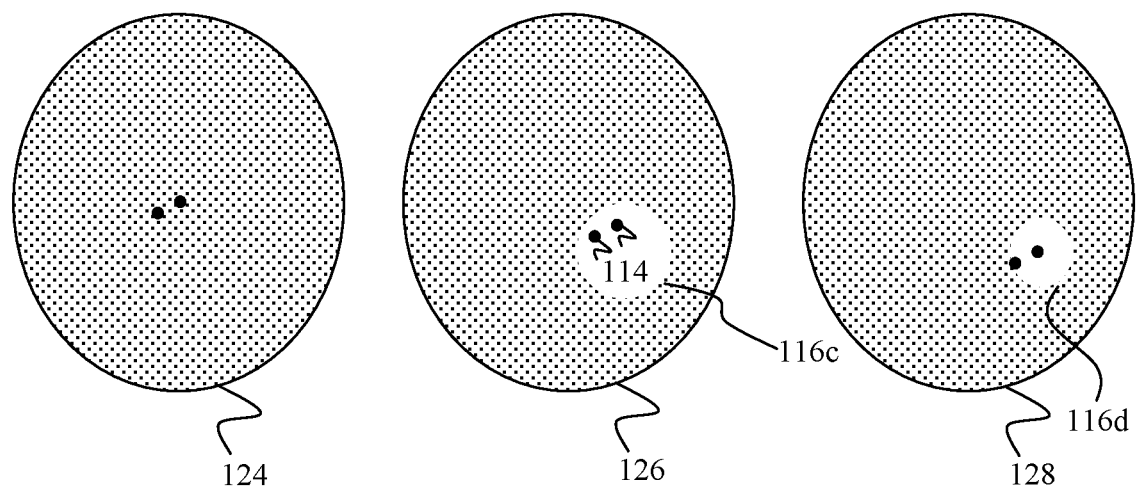
FIG. 2D depicts test data corresponding to treatment of a tumor by an embodiment.

Referring now to FIG. 2C, an example lead 118 is depicted. Lead 118 is configured as a bipolar electrode enclosed in insulated tubing with only the tip 120 of the each of the positive electrode and negative electrode touching the base of the plate 122. FIG. 2D depicts a top view of lead 118 in use in an in vitro environment. Plates 124, 126, and 128 each depict a 35 mm cell culture dish showing crystal violet staining of tumor cells after a specific duration of electric field. Control plate 124 is fitted with an electrode without an active electric field, with active electrode portions 114. Test plates 126 and 128 show results of an active electrode delivering waveforms at 100 Hz (plate 126) and 200 kHz (plate 128). Cleared zones 116c and 116d demonstrate tumor cell death in the vicinity of active electrode portions 114.

For the data shown in FIGS. 2D, a temperature sensor probe was used to record the rise in temperature of the culture media, if any, between the two electrodes. The temperature was recorded between the two electrodes after the delivery of electric field for a specific duration, and it was found that the temperature was of the order of 39.4 degrees C., which is well within the physiological limit suggesting there is no non-specific thermal effect of electric field.

Figure 3A:
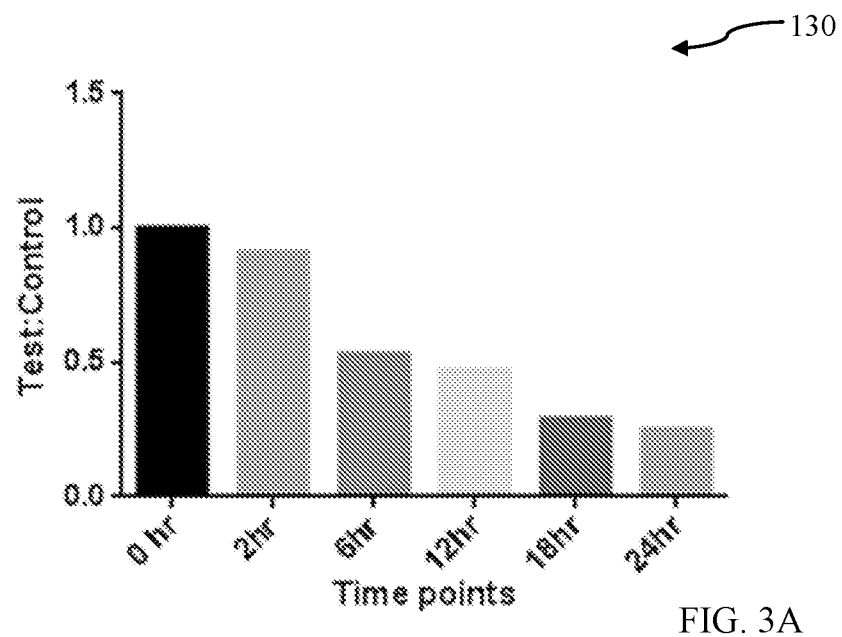
FIG. 3A depicts test data corresponding to treatment of tumor cells according to an embodiment.

FIG. 3A depicts a graph 130 demonstrating progressive decrease in tumor cell counts over time after application of an electric field using lead 118. Using a ratio of hand counted cells between a test plate and a control plate, the steady decrease in the test plate count leads to a marked decline in the ratio over 24 hrs. The ratio declines sharply over the first six hours or so, before gradually appearing to level out roughly between the 18 and 24 hour mark, exemplifying the tendency, and capacity, of tumor cells to mutate immunities to therapeutic methods.

Figure 3B:
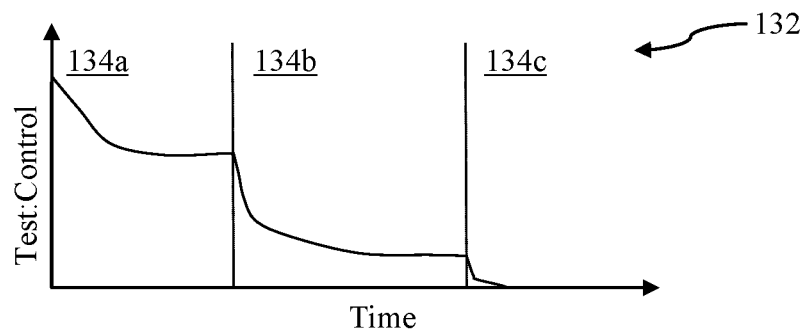
FIG. 3B is an example decay curve depicting the multi-drug-analogous treatment model, according to an embodiment.

FIG. 3B shows an example graph 132 of application of the methods and systems of the present disclosure using a "multi-drug" methodology. Section 134a follows approximately the same model as graph 130 of FIG. 3A. When the decline in tumor size plateaus, the parameters of the applied electronic field may be adjusted to drive further recession of the tumor, demonstrated in segment 134b. This may be repeated iteratively until no further tumor cells are detected, demonstrated in segment 134c.

Electrical stimulation can initiate a process of cell death and disrupt cancer cell growth, which can inhibit tumor growth. Micrographs of cells approximately 24 hours after application of electric stimulation delivered according to the systems and methods discussed herein show decreased density of cells in comparison to the control samples when stained with crystal violet, which demonstrates that there is a process of cell death that initiates after electric stimulation. Micrographs of cells 48 hours after electric stimulation, when stained with crystal violet, show almost no viable adherent tumor cells in comparison to the control samples, which further demonstrates that a process of cell death initiates after electric stimulation. Micrographs of cells 48 hours after electric stimulation, when stained with crystal violet, show almost no viable adherent tumor cells in comparison to the control samples, which further demonstrates that a process of cell death initiates after electric stimulation.

Figure 4A:
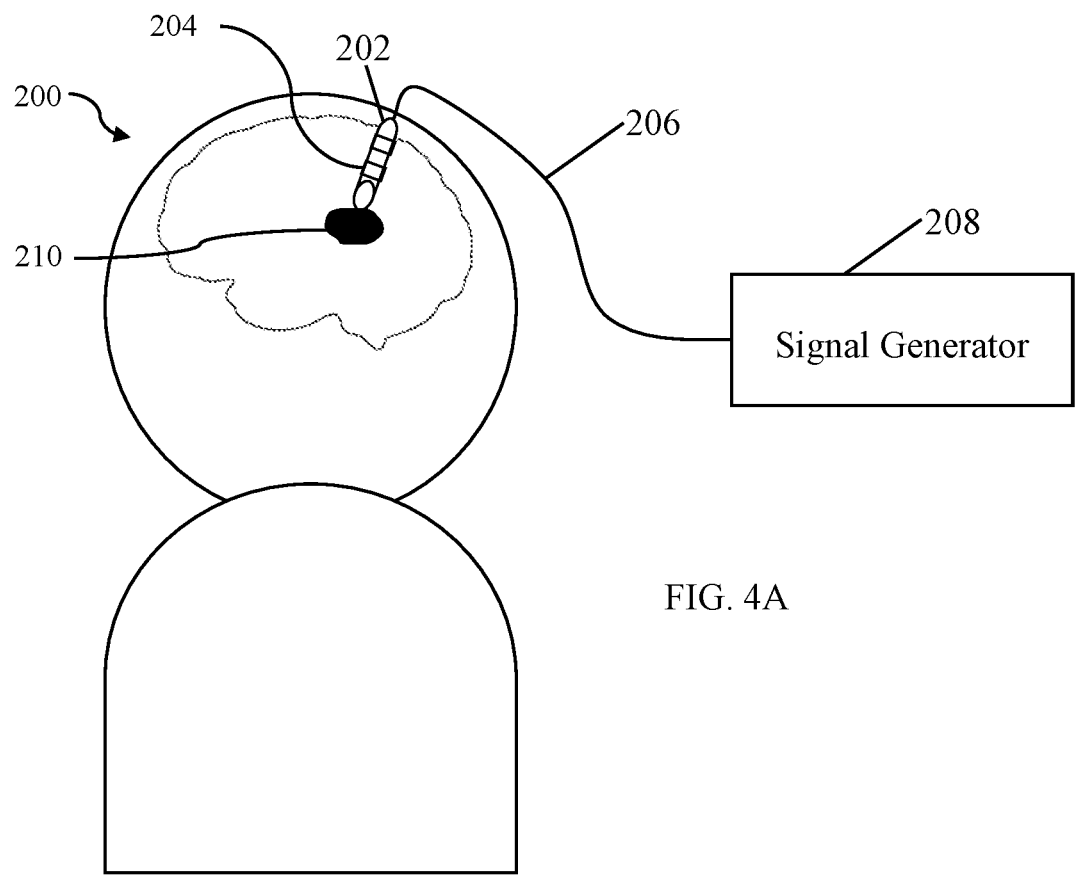
FIG. 4A is a schematic side view depicting a lead implanted in the tumor of a patient according to an embodiment.

FIG. 4A depicts an example of a DBS system 200 for disruption of tumor proliferation processes. DBS system 200 includes at least one lead 202 comprising one or more electrodes 204. Generally, the exterior surface of lead 202 comprises a non-conductive material while each electrode 204 comprises an electrically conductive material. For example, in one embodiment lead 202 comprises a polyurethane sleeve, and electrode 204 comprises platinum-iridium. Other suitable materials or combinations of materials can be used for one or both of lead 202 and electrode 204 in other embodiments. Lead 202 is in electrical connection via an extension 206 (e.g., a cord, cable, wire or other structure in some embodiments, or a wireless arrangement in other embodiments) to a signal generator 208. In embodiments, signal generator 208 can be implanted or external. In other embodiments, DBS system 200 can comprise more than one lead 202, directed to one or more tumors or areas of interest. The number of leads may be determined according to the particular geometry and distribution of the target tissue.

In operation, system 200 provides tumor-specific, therapeutic electrical signals generated by signal generator 208 to create an electric field within and around a tumor 210 or other treatment area by lead 202 and electrodes 204. The electric field can trigger metabolic pathways in the tumor or other tissue at a cellular level to provide a therapeutic effect, as discussed in more detail herein. Interactions of the field with charged particles of the cells of the tumor can both directly damage the cellular structures of the tumor and assist the patient's recovery.

Figure 4B:
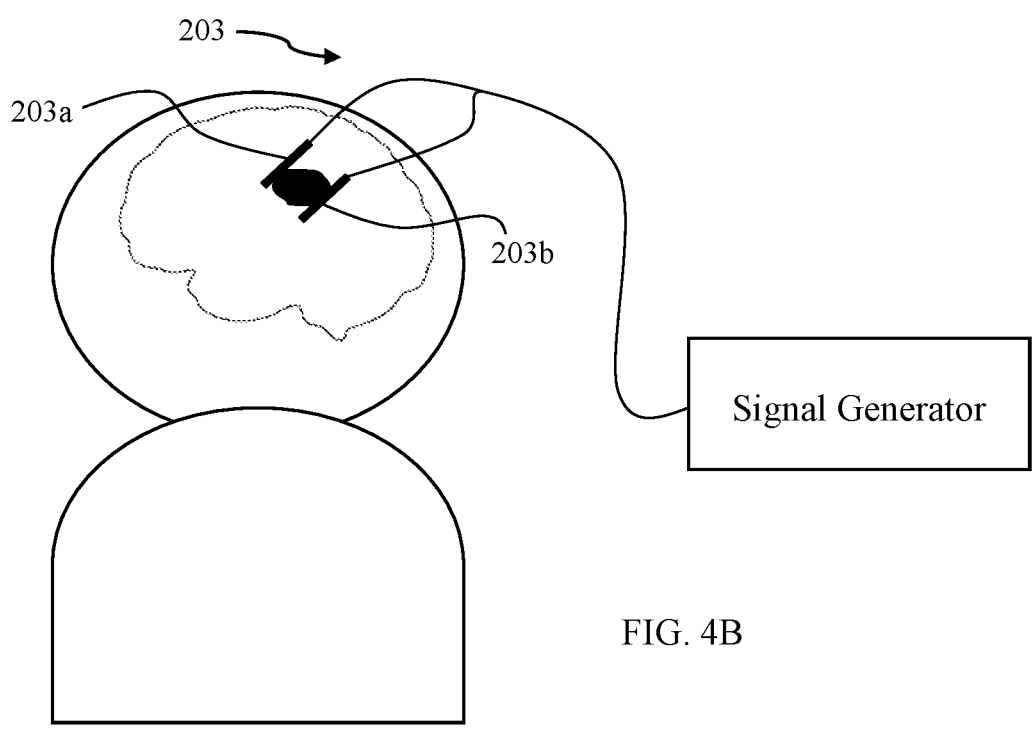
FIG. 4B is a schematic side view depicting two leads implanted in the tumor of a patient according to an embodiment.

Referring now to FIG. 4B, an alternative embodiment of system 200 is shown with a dual lead 203 configuration. FIG. 4B depicts leads 203A and 203B implant adjacent and on either side of tumor 210. Leads 203A and 203B are similar to leads 118a and 118b of FIG. 2C. Placing bilateral leads 203A and 203B to bookend tumor 210 allows for the electric field generated by leads 203 to be distributed across tumor 210.

Figure 4C:
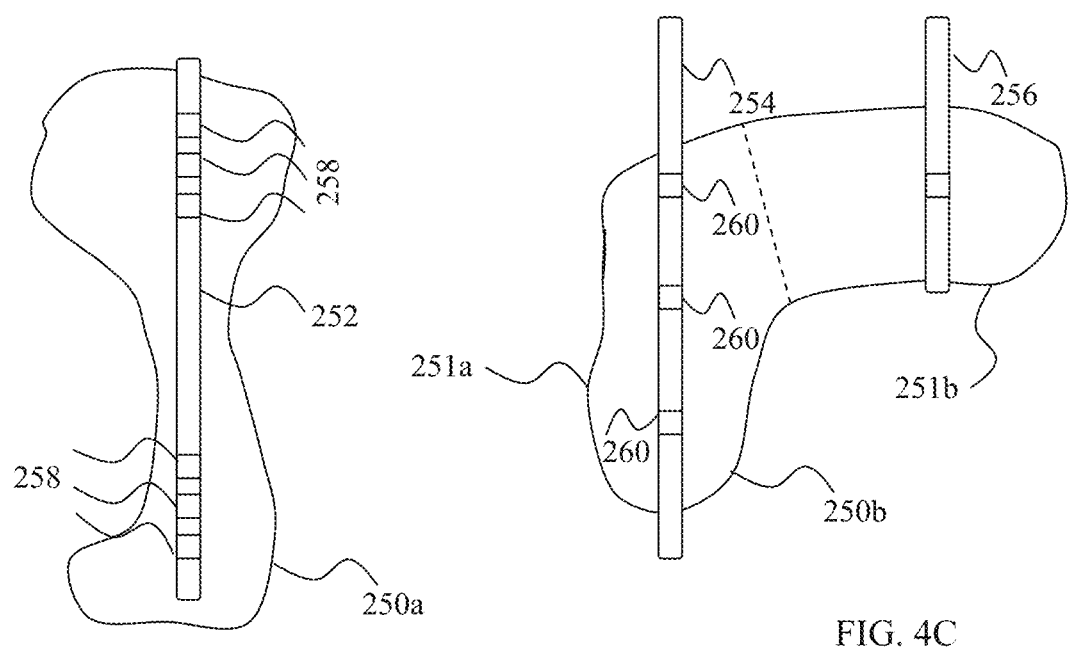
FIG. 4C depicts customized leads for tumor ablation according to two embodiments.

Referring now to FIG. 4C, examples of custom leads to accommodate irregular tumor shapes is depicted. Tumors 250a and 250b each have a unique geometry, and each of leads 252, 254, and 256 are customized to direct an electromagnetic field over the particular geometry of either tumor 250a or 250b. Lead 252 has electrodes 258 clustered at either end of the lead 252 to direct the field over the large lobes of tumor 250a. Tumor 250b, on the other hand, can be treated as two connected units, 251a and 251b, to create a more conforming EM field over the irregular shape of tumor 250b and limit any potential effects on healthy tissue. Lead 254 has regularly spaced electrodes 260 to cover the larger unit 251a, and a second lead 256 provides coverage over the second unit 251b.

Figure 5A:
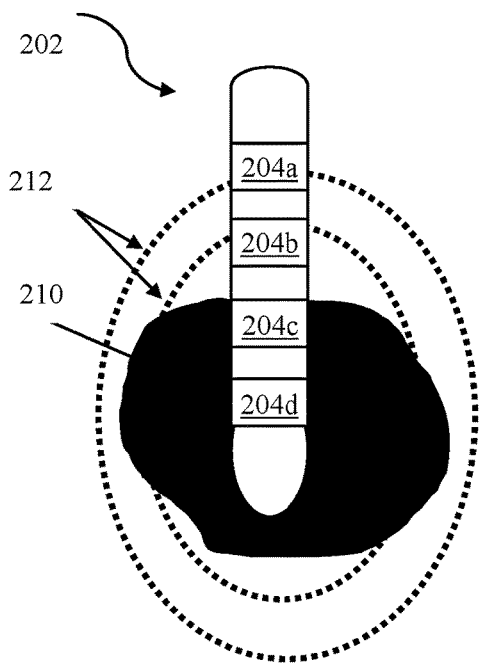
FIG. 5A is a schematic view depicting a lead with four electrodes, and the electric field/VTA produced by the configuration, according to an embodiment.

Leads 202 and 203 can comprise various electrode configurations. FIG. 5A depicts one electrode configuration in which lead 202 comprises four circumpolar electrodes 204a-d. A lead with four circumpolar electrodes, such as the lead shown in FIG. 5A can produce a non-specific electric field 212 that extends beyond tumor 210. Such non-specific fields may be particularly advantageous in ensuring the elimination of any malignant cells which may have spread from the main tumor.

Figure 5B:
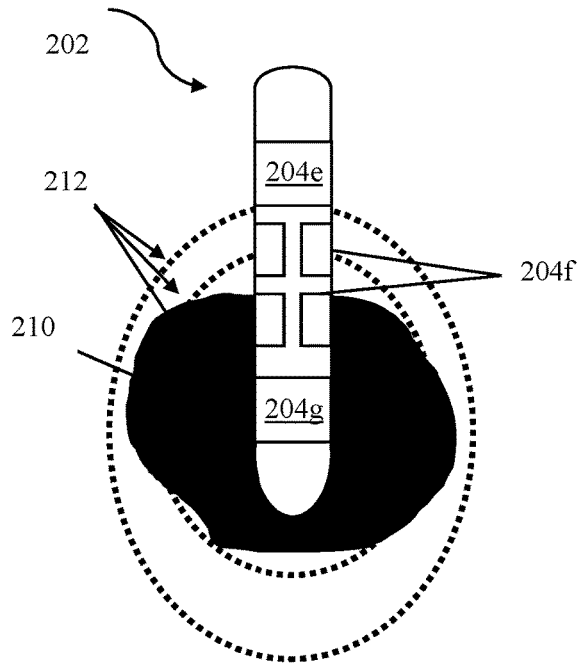
FIG. 5B is a schematic view depicting a lead with eight electrodes, and the electric field/VTA produced by the configuration, according to an embodiment.

FIG. 5B depicts a single, triple, triple, single electrode configuration. In this configuration, lead 202 comprises eight electrodes (204e-g): electrodes 204e and 204g are circumpolar ("single") electrodes, and electrodes 204f are two rows of three electrodes ("triple") surrounding the lead (only two electrodes of each row are visible in FIG. 5B). As depicted in FIG. 5B, a single, triple, triple, single electrode configuration can produce a non-specific electric field 212 that is contoured to tumor 210. Contouring the field may assist in focusing effects on a particular tumor or tumor region and may be advantageous in embodiments used in regions of the body outside the central nervous system. Since cells in other systems generally divide with greater frequency than mature neurons, embodiments designed for applications in other systems may use field contouring to limit the risk of adverse effects on healthy tissue.

Figure 5C:
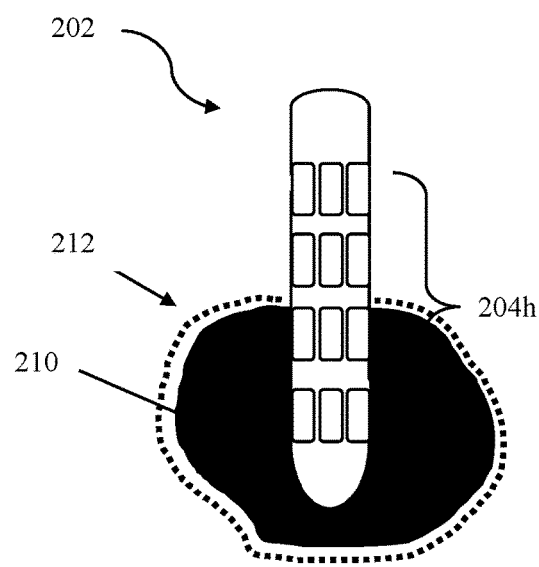
FIG. 5C is a schematic view depicting a lead with a custom electrode arrangement, and the electric field/VTA produced by the configuration, according to an embodiment.

FIG. 5C depicts another electrode configuration in which lead 202 comprises an array of electrodes 204h arranged in multiple rows around lead 202. As depicted in FIG. 5C, the array of electrodes arranged in multiple rows around lead 202 can produce an electric field that conforms specifically to a boundary of tumor 210. Such conformation is a more precise version of the contouring discussed in regard to FIG. 5B, and carries many of the same advantages. For instance, for tumors of the gastrointestinal (GI) system, where the turnover of healthy cells is relatively high, such a precisely conforming field would permit treatment of a tumor without damaging the patient's healthy GI tissue and therefore avoiding digestive complications.

FIGS. 5A-5C are only some examples of suitable lead configurations and electric fields. Other configurations, arrangements and types of leads that produce other electric fields can be used in various embodiments discussed herein. Leads may be prefabricated or assembled according to the determined configuration using prefabricated or customized electrodes. Customization of leads and/or electrodes may vary in execution, from assembling existing electrodes into a customized lead, implanting customized electrodes into an existing lead assembly, or fully fabricating a complete custom lead and electrode assembly, for example through the use of 3D printing.

Custom contacts of lead 202 and electrodes 204 can be of varying shape and distance from each other depending on the desired electric field/VTA. Electrical parameters that can be customized include one or more of amplitude, pulse width, frequency, waveform/pulse shape, pulse pattern, or burst. VTAs can also be shaped by preconditioning pulses or field orientation.

Figure 6:
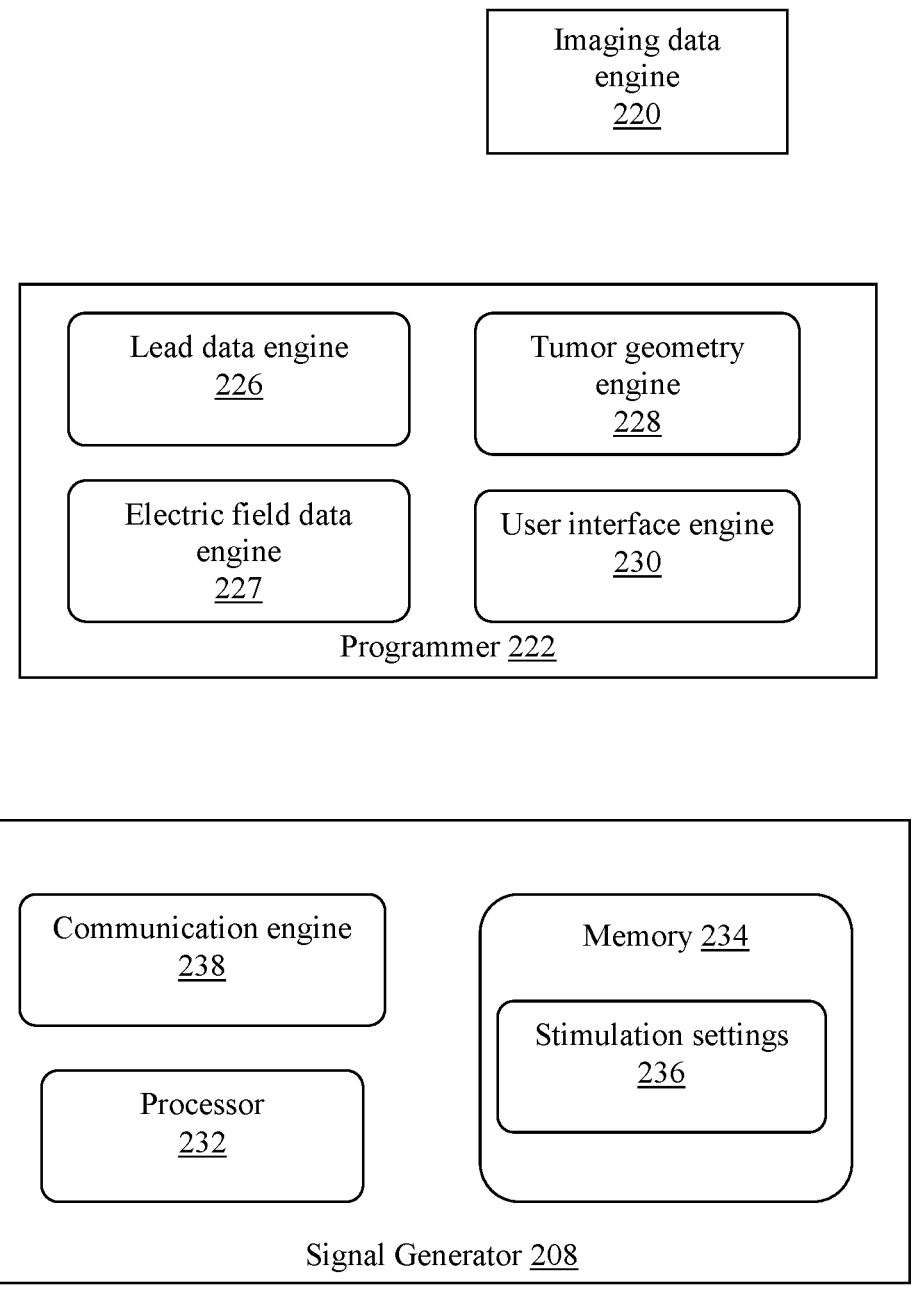
FIG. 6 is a block diagram of an imaging, treatment design, and signal generation system according to an embodiment.

In operation, lead 202 (and thereby electrodes 204) receives electrical signals from signal generator 208 via extension 206 (see FIG. 4A). In one embodiment, and referring to FIG. 6, signal generator 208 comprises a processor 232 and a memory 234. Memory 234 can include storage for stimulation settings 236, such as stimulation settings for each electrode 204 of lead 202.

Stimulation settings 236 can be generated by processor 232 or by an external source and can comprise, for example, an array, hash table, dictionary, database or other data structure keyed to each electrode 204. In one example, stimulation settings 236 can define a modulated, pulsed signal that establishes an electric field in a tumor. The stimulation settings can define a frequency (e.g., low, medium, high, or ultra high), a pulse width or time, a pulse interval, a pulse pattern, a pulse waveform shape (e.g., sine-type or square-wave pulse), a current type (e.g., AC vs. DC), a voltage, a power, or some other characteristic of a signal to establish a desired electric field.

Stimulation settings 236 can produce electrical signals that are communicated from signal generator 208 to lead 202 via extension 206 by communication engine 238, which can comprise wired or wireless communication circuitry. In embodiments in which stimulation settings 236 are at least partially formulated external to signal generator 208, communication engine 238 can receive stimulation settings 236 stored within memory 236, or alternatively can receive similar information and settings directly from a programmer 222. In still other embodiments, signal generator 208 and programmer 222 can comprise an integrated unit.

Programmer 222 comprises, among other components appreciated by those skilled in the art, a lead data engine 226, an electric field data engine 227, a tumor geometry engine 228 and a user interface engine 230. Programmer 222 can be a handheld device, laptop or desktop computer, server, tablet, cellular or smart phone or other computing device capable of data communication with signal generator 208. Lead data engine 226 is configured to obtain or formulate data related to lead 202, such as a particular configuration of electrodes 204. Electric field data engine 227 is configured to obtain or formulate data related to electrical signals to be generated and provided to lead 202, such as a particular set of signal characteristics tailored for a particular tumor. In combination, the particular configuration of electrodes 204 and electrical signals provided to lead 202 (and thereby electrodes 204) produce a desired electrical field to be applied to a tumor or other target tissue when lead 202 is implanted in the tumor or other target tissue.

Both lead data engine 226 and electric field data engine 227 can rely on data from tumor geometry and density engine 228, which is configured to generate or obtain data related to a tumor or tissue to be treated. In one embodiment, tumor geometry engine 228 receives, via wired or wireless communications, tumor data from an imagine data engine 220. This data can be, for example, three-dimensional magnetic resonance imaging (3D MRI) data, though in other embodiments other data can be used, such as two-dimensional MRI data or three- or two-dimensional data from another imaging modality (e.g., a computed tomography, or CT, scan, or a position emission tomography, or PET, scan, among other possibly modalities). Imaging data obtained or provided by imaging data engine 220 can be used by programmer 222 (or signal generator 208) to design a tumor-specific electric field to be produced by signals generated by signal generator 208 and communicated to lead 202 and electrodes 204 implanted within a tumor. In particular, imaging data can be used to identify a target volume of tissue activation (VTA) such that appropriate leads, electrodes and stimulation parameters can be designed and selected.

Engines 226, 227, 228 and 230 can comprise software, firmware, hardware or combinations thereof and can comprise or be controlled, executed or coupled by a processor or other computing device. In still other embodiments, engines 226, 227, 228 and 230 can comprise different functions, routines, algorithms or functional units of a processor or other device. Other components of the devices depicted in FIG. 6, including hardware and software components, can be included even if they are specifically depicted.

Figure 7A:
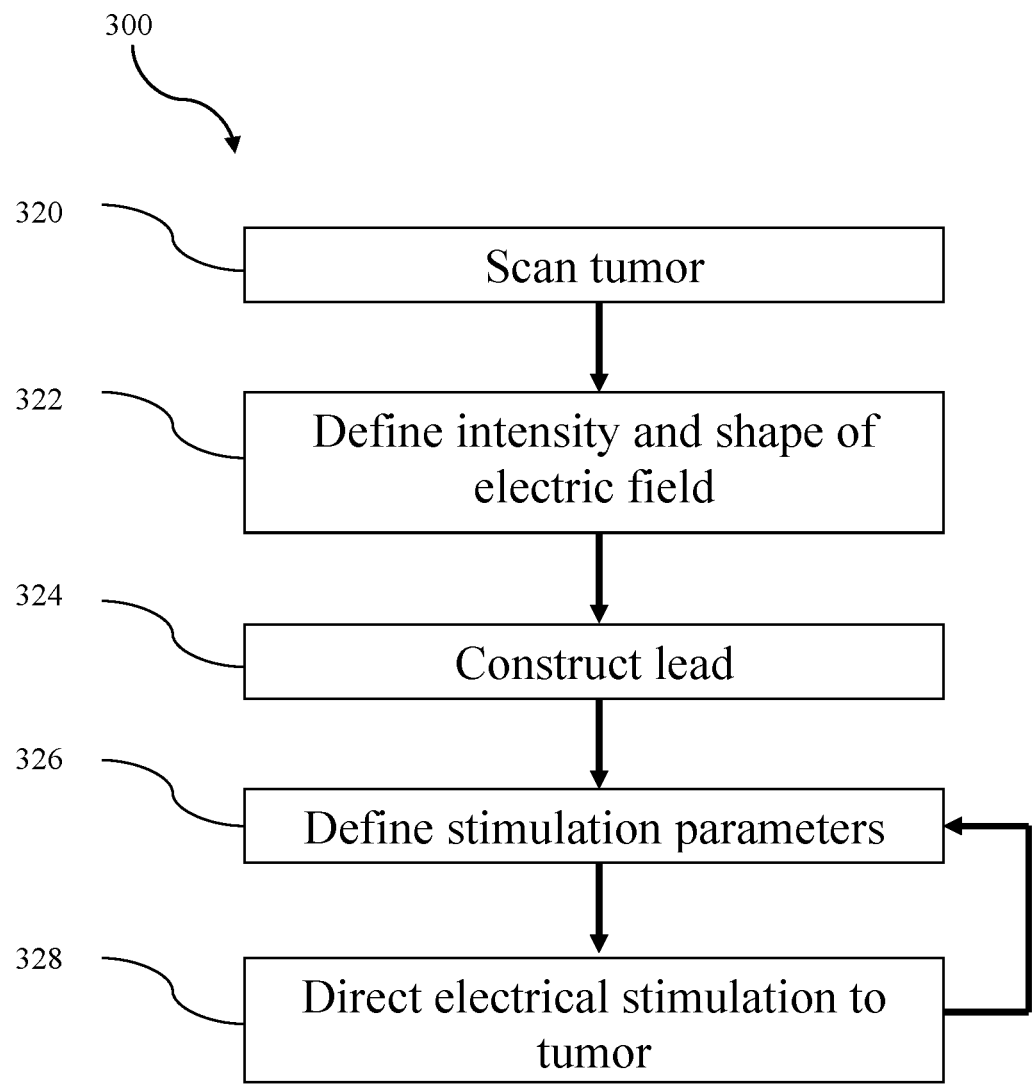
FIG. 7A is a flowchart of a method for performing direct electrode stimulation of cancerous tissue in a patient, according to an embodiment.

FIG. 7A is a flowchart of a method by which an electrode configuration can be selected and signal generator can be programmed to deliver a specific set of stimulation parameters to the patient.

At 320, a tumor is scanned with an imaging data engine in order to acquire tumor data. In one embodiment, the tumor data comprises information regarding one or more of tumor shape, location, density, size, or volume. At 322, the tumor data can be communicated to a programmer. The programmer can model the tumor via a tumor geometry engine. The programmer can then use electric field data engine to model an electric field to be targeted to the tumor based on the tumor data. The programmer can utilize a lead data engine to design, model or select a lead based on the electric field model. The configuration of electrodes on the lead, along with the signal provided according to the electric field, will define the shape and other characteristics of the electric field generated and delivered to the tumor.

At 324, a lead, as designed, modeled, or selected by the programmer, is obtained or constructed. Further, at 326, the signal generator is programmed by the programmer with stimulation settings based on the modeled electric field. The stimulation parameters define the intensity and dynamics of the electric field. Such parameters can be adjusted by programmer to disrupt the various processes of tumor cancer cell growth.

Accordingly, embodiments of the systems and methods herein can be considered to deliver a "multi-drug" that selectively targets one or more processes of the tumor in a therapeutically beneficial way, thereby inhibiting tumor growth. If or as the tumor responds, the multi-drug can be tuned (i.e., one or more characteristics of the lead, electrodes, or stimulation settings defining the electric field can be adjusted according to the tumor's response) accordingly. The field can thus be programmed to proactively address the rapid desensitization that some tumors exhibit in the course of therapy, wherein a drug or regimen will abruptly cease to be effective due to mutation of the tumor genome. By applying a mixed- or cycling-effect field (or "multi-drug"), the possibility of a mutation arising in the tumor which may permit it to survive the treatment, as any mutation that renders the tumor resistant to a particular effect of the field will likely leave it vulnerable to other effects.

For example, a tumor may initially be treated with a low frequency waveform to interfere with the stability of mitotic division. If the tumor fails to respond, or responds and then plateaus, the stimulation setting may be adjusted to treat the tumor with a high frequency waveform instead. In particular, tumors that are especially large, cross-sectionally diverse, or otherwise malignant may invite treatment of mixed frequencies (or other features), either overlapping or cycling as part of the initial stimulation pattern. In some situations, there can be more than one combination of lead(s), electrodes and stimulation parameters that can result from the model (from which a user may select or according to which a preferred or optimized combination can be recommended), while in others a single optimized combination of lead(s), electrodes and stimulation parameters can result.

At 328, a lead is implanted directly adjacent to the tumor of interest, and the signal generator directs stimulation parameters to the lead. Implanting the lead directly adjacent to tumor provides several advantages, including being able to target the electric field directly at and into the tissue of interest, which can minimize the potential for adverse effects on healthy tissue around the tumor. In some embodiments, electrical stimulation can be applied repeatedly in order to apply a sequence or range of stimulation parameters that will disrupt targeted processes. This repetition can be close in time (e.g., spaced apart by seconds or minutes) or farther apart (e.g., repeated daily, weekly, monthly or according to some other period), or even simultaneously, or randomly, to prevent accommodation or adaptation to the therapy and produce a more robust effect.

In other embodiments, more or fewer activities can be carried out as part of the method, such that additional activities not depicted in FIG. 7A can be included, or activities that are depicted can be reordered or omitted. For instance, in the case of especially large brain tumors, treatment may begin with surgical resection to release cranial pressure, and lead implantation can occur concurrent or subsequent to the resection.

In various embodiments, embodiments of the devices and systems discussed herein can be used to obtain a three-dimensional model of a tumor or other target tissue, define a desired volume of tissue activation based on the three-dimensional model, select an appropriate lead and electrode configuration for the desired volume tissue activation, and a define characteristics of an electric field to be established by the lead and electrode configuration when the lead is implanted within the tumor or other target tissue to deliver the electric field therein. After one or more treatments, these activities can be repeated, with one or more of the lead, electrodes or electric field characteristics adjusted according to the particular response of the tumor or other tissue (which can be determined by re-imaging or using other techniques (e.g., analyzing patient symptoms and correlating symptoms with imaging data to obtain a patient positive effect score) to characterize the tumor or tissue.

Figure 7B:
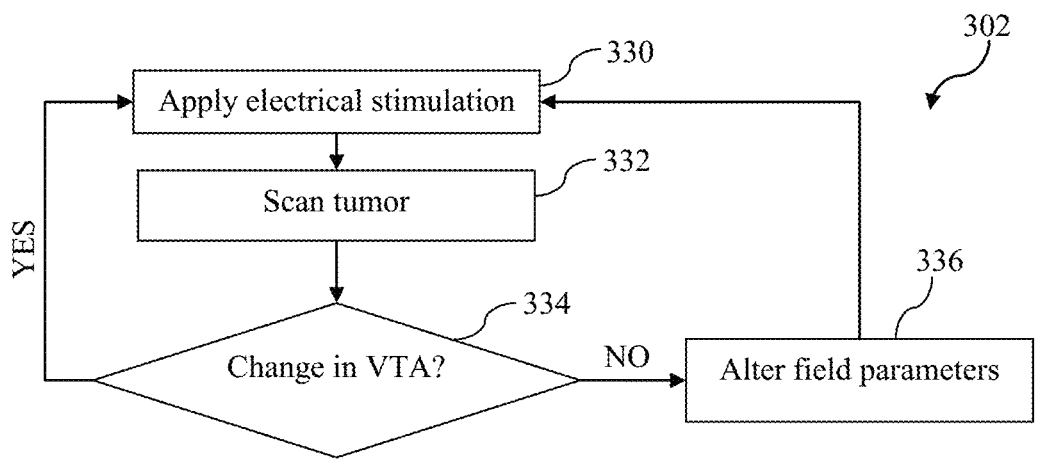
FIG. 7B is a flowchart of a method for performing multi-drug-analogous treatment using electromagnetic field, according to an embodiment.

FIG. 7B shows flowchart 302 of a method for using the systems and devices of the present disclosure for a "multi-drug" treatment regimen. At operation 330, an initial electrical stimulation is applied, according to the VTA determined from an initial scan. After treatment at the initial stimulation setting has been completed for the determined duration, the tumor is scanned again, as at operation 332. A new VTA is calculated from the new scan and compared with the initial VTA, as at decision block 334. If change is detected, the treatment is continued according to the current settings, at operation 330.

However, if no change is detected, the tumor can be determined to be unresponsive to the current treatment, and the parameters of the field may be altered, as at operation 336. Parameters may be altered to adjust the mode of attack, e.g., by change the frequency, or intensity of the treatment, e.g., by decreasing the pulsewidth. Once the new parameters are entered, treatment is resumed by the applying the electrical stimulation, at operation 330. Method 302 may continue iteratively until the tumor is sufficient reduced.

Thus, the systems and methods discussed herein can be considered to be a "smart multi-drug" that can be used to target and treat various tumors and tissues and selectively adapt according to a particular effect desired or actual response of the tumor or tissue. Such smart multi-drugs can be used to treat a variety of tumors and cancers as well as other conditions (e.g., inflammation). The particular conditions, frequencies, and other characteristics given herein are merely examples of some possibilities and are not limiting with respect to the applicability of various contemplated embodiments.

For instance, the example and embodiments discussed herein are largely directed to treatment in particular of GBM in the brain. However, other embodiments follow naturally from the technology described herein. Tumors of the spinal cord, which do not permit direct implantation of electrodes due to the narrow confines of the spinal column, could be treated with epidural leads. Melanoma and other cancers of the skin could be treated with such epidural leads as well. Osteosarcoma and other bone tumors could be treated without the severe side effects of radiation or systemic chemotherapy. Blood cancers could be treated with ventricular filters fitted to deliver an electric field to passing blood cells and thus attack tumors of the blood.

Figure 8A:
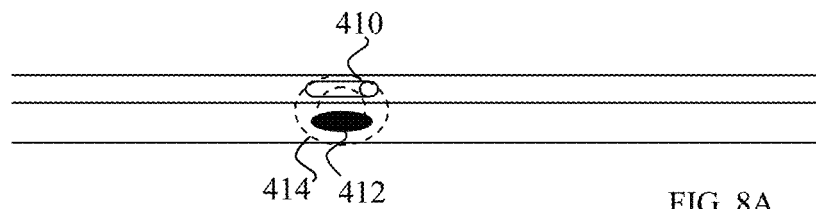
FIGS. 8A and 8B depict a venous tumor trap, according to an embodiment.

Referring now to FIG. 8A, an alternative embodiment demonstrating the use of an epidural lead 410 to treat a spinal tumor 412 is depicted. Though the narrow confines of the spinal column make implantation into the spine difficult, a lead implanted adjacent to the spine is able to project a field 414 across the tumor in the spine to effect treatment.

Figure 8B:
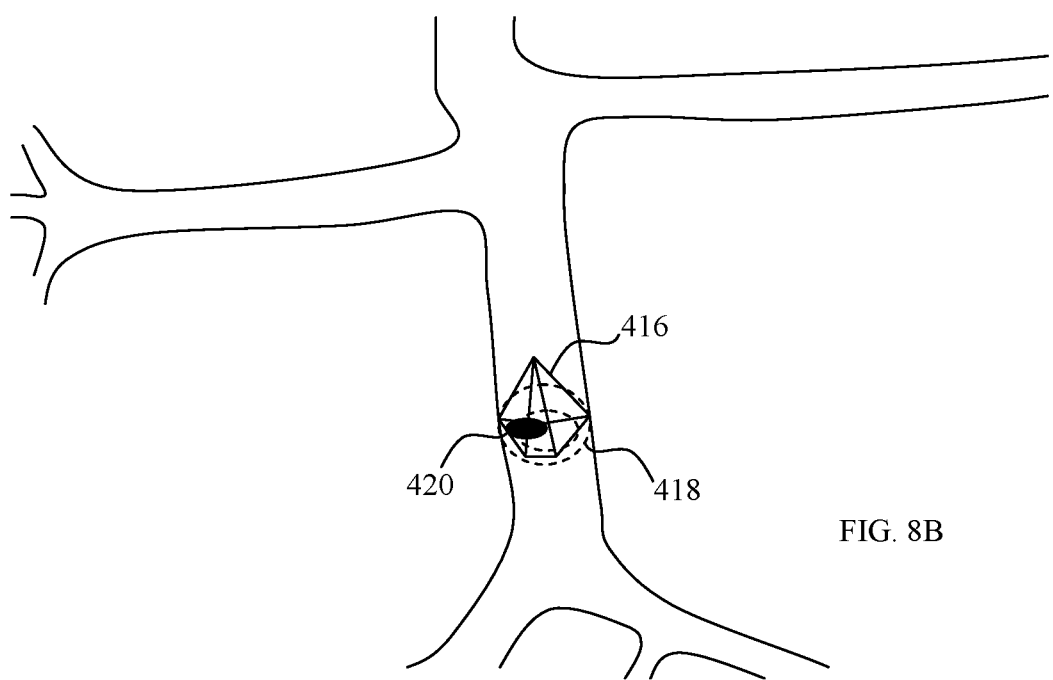

FIG. 8B depicts an alternative embodiment demonstrating use of venous filter 416 to project filed 418 and capture blood tumor 420 for exposure to the field. Venous filter 416 can have attached leads to project field 418, or field 418 may be projected by leads implanted in adjacent epidural or other tissue. Venous filter 416 captures blood cancer tumor 420 and retains the tumor 420 within the field 418 to effect treatment.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

IV. Discussion of Specific Claimed Embodiments

In one embodiment, a signal generator is electronically coupled to a plurality of electrodes. The signal generator comprises a processor configured to receive a set of tumor-specific electromagnetic field data and generate a corresponding set of stimulation settings, wherein the set of stimulation settings comprise a specific output setting for each of the plurality of electrodes; a memory configured to receive and store the set of stimulation settings from the processor; and a communication engine configured to deliver the specific output settings to each corresponding one of the plurality of electrodes to generate a tumor-specific electromagnetic field based upon to the tumor-specific electromagnetic field data. The specific output settings include a set of electrical parameters based upon the tumor-specific electromagnetic field data.

The processor may be configured to receive the tumor-specific field data from a programmer module and generate the set of stimulation settings based on a tumor profile and a desired effect on the tumor. The tumor profile may be produced based on a tumor type and a three-dimensional model of the tumor. The programmer module may in fact be a part of the signal generator itself. The processor may be configured to receive one or more electrode configurations. The the one or more electrode configurations may be received from a programmer module and based on a tumor profile and a desired effect on the tumor. The one or more electrode configurations comprise an array of the plurality of electrodes on an implantation lead. The one or more electrode configurations may be selected from readily available implantation leads based on the profile and a desired effect on the tumor. The implantation lead may configured for implantation in a brain of a patient. The implantation lead may be configured for epidural implantation. The lead may be integrated with a venous filter. The one or more electrode configurations may be customized based on the profile and a desired effect on the tumor. The implantation lead may include one of the one or more electrode configurations and can be generated through 3D printing or other additive or custom manufacturing processes. The one or more electrode configurations can be obtained using a computer-implemented algorithm. The electrode configuration can include two or more electrodes and each of the two or more electrodes is stimulated with a different one or more of the one or more stimulation settings. The one or more sets of stimulation settings can be obtained using a computer-implemented algorithm, which can include machine-learning or neural network based algorithms. The one or more sets of stimulation settings can be delivered simultaneously or sequentially. The one or more sets of stimulation settings can be delivered cyclically or randomly. The one or more sets of stimulation settings can be delivered by alternating among the one or more sets of stimulation settings. A first set of the one or more sets of stimulation settings may targets mitosis inhibition, wherein one of the stimulation parameters included in the first set is frequency, and wherein the frequency is in a range of 61 Hz to 200 Hz. A second set of the one or more sets of stimulation settings may target immune suppression, wherein one of the stimulation parameters included in the second set is frequency, and wherein the frequency is in a range of 300 Hz to 700 Hz. A third set of the one or more sets of stimulation settings can target inhibition of DNA replication, wherein one of the stimulation parameters included in the third set is frequency, and wherein the frequency is equal to or greater than 1,000 Hz. The processor can be further configured to receive a second set of tumor-specific electromagnetic field data and generate a second corresponding set of stimulation settings. The second set of tumor-specific electromagnetic field data can be based on a first tumor profile, a second tumor profile, and a rate of change of the of the tumor profile based on the first tumor profile and the second tumor profile.

It should be understood that many of these features are interoperable with one another. For example, using different sets of inhibition waveforms sequentially or simultaneously are interoperable features.

According to another claimed embodiment, an electrical stimulation system comprises a programmer module configured to receive imaging data for a target tissue and to generate a profile of the target tissue, wherein the programmer module is configured to generate one or more sets of stimulation settings based on the profile and a desired volume of tissue activation (VTA) of the target tissue; a signal generator configured to generate electrical stimulation signals according to the one or more sets of stimulation settings; and one or more leads each comprising one or more electrodes, the one or more deep brain stimulation leads electrically coupled with the signal generator to receive the electrical stimulation signals and to apply an electric field to the target tissue when implanted within the target tissue.

In embodiments, each of the one or more leads is a deep brain stimulation lead. Each of the one or more leads may be a epidural implantation lead. Each of the one or more leads may be integrated with a venous filter. The programmer module may be configured to generate an electric field model based on the profile and the desired VTA of the target tissue, and the programmer module may use the electric field model to generate the one or more sets of stimulation settings. The programmer module may generate one or more configurations of the one or more electrodes on the one or more leads based on the electric field model. The programmer may selects the one or more configurations from a set of available leads. The programmer module can select a custom electrode configuration. The signal generator can deliver the one or more sets of stimulation settings simultaneously, cyclically, or randomly. The signal generator can deliver the one or more sets of stimulation settings by alternating the one or more sets of stimulation settings. The programmer module can receive a second set of imaging data for the target tissue after the electric field is applied to the target tissue and in response the programmer module generates a second profile of the target tissue and a second one or more sets of stimulation settings based on the second set of imaging data and a corresponding desired VTA.

As described previously, these features are interoperable with one another, and a skilled person would recognize that they can be combined in various combinations and permutations.

According to another embodiment, a signal generator comprises a processor. The processor is configured to produce an output based upon a first set of electrical parameters corresponding to a first cell cell proliferation process; receive tumor image data; determine whether the tumor image data is indicative of minimal change in Volume of Tumor Activation (VTA) over time; and, in response to the determination that the tumor image data is indicative of minimal change in VTA, produce an output based upon a second set of electrical parameters corresponding to a second cell proliferation process.

The signal generator further include an electrode, the electrode configured to deliver an electromagnetic signal to a tumor based upon the first set of electrical parameters and upon the second set of electrical parameters.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A signal generator electronically coupled to a plurality of electrodes, the signal generator comprising:
   a processor configured to:
      receive a first set of tumor-specific electromagnetic field data and generate a first corresponding set of stimulation settings, and
      receive a second set of tumor-specific electromagnetic field data and generate a second corresponding set of stimulation settings based on a first tumor profile, a second tumor profile, and a size or a rate of change of the tumor profile and based on the first tumor profile and the second tumor profile,
      wherein the first and second sets of stimulation settings each comprise a specific output setting for each of the plurality of electrodes;
   a memory configured to receive and store the set of stimulation settings from the processor; and
   a communication engine configured to deliver the specific output settings to each corresponding one of the plurality of electrodes to generate a tumor-specific electromagnetic field based upon to the tumor-specific electromagnetic field data,
   wherein the specific output settings include a set of electrical parameters based upon the tumor-specific electromagnetic field data.

2. The signal generator of claim 1, wherein the processor is configured to receive the first tumor-specific electromagnetic field data from a programmer module and generate the first set of stimulation settings based on the first tumor profile and a desired effect on the tumor.

3. The signal generator of claim 2, wherein the first tumor profile is produced based on a tumor type and a three-dimensional model of the tumor.

4. The signal generator of claim 2, further comprising the programmer module.

5. The signal generator of claim 1, wherein the one or more sets of stimulation settings are:
   obtained using a computer-implemented algorithm,
   delivered simultaneously,
   delivered cyclically or randomly, or
   delivered by alternating among the one or more sets of stimulation settings.

6. The signal generator of claim 1, wherein a first set of the one or more sets of stimulation settings targets mitosis inhibition, wherein one of the stimulation parameters included in the first set is frequency, and wherein the frequency is in a range of 61 Hz to 200 Hz.

7. The signal generator of claim 1, wherein a second set of the one or more sets of stimulation settings targets immune suppression, wherein one of the stimulation parameters included in the second set is frequency, and wherein frequency is in a range of 300 Hz to 700 Hz.

8. The signal generator of claim 1, wherein a third set of the one or more sets of stimulation settings targets inhibition of DNA replication, wherein one of the stimulation parameters included in the third set is frequency, and wherein the frequency is equal to or greater than 1,000 Hz.

9. The signal generator of claim 1, the processor further configured to receive a second set of tumor-specific electromagnetic field data and generate a second corresponding set of stimulation settings.

10. The signal generator of claim 9, the second set of tumor-specific electromagnetic field data based on a first tumor profile, a second tumor profile, and a rate of change of the of the tumor profile based on the first tumor profile and the second tumor profile.

11. A signal generator electronically coupled to a plurality of electrodes arranged on an implantation lead, the signal generator comprising:
   a processor configured to receive a set of tumor-specific electromagnetic field data and generate a corresponding set of stimulation settings, wherein the set of stimulation settings each comprise a specific output setting for each of the plurality of electrodes in an electrode configuration;
   a memory configured to receive and store the set of stimulation settings from the processor; and
   a communication engine configured to deliver the specific output settings to each corresponding one of the plurality of electrodes to generate a tumor-specific electromagnetic field based upon to the tumor-specific electromagnetic field data,
   wherein the electrode configurations are received by the processor from a programmer module and based on a tumor profile and a desired effect on the tumor or obtained using a computer-implemented algorithm and are customized based on the profile and a desired effect on the tumor;
   wherein the specific output settings include a set of electrical parameters based upon the tumor-specific electromagnetic field data; and
   wherein the implantation lead includes one of the one or more electrode configurations and is generated through 3D printing.

12. The signal generator of claim 11, wherein the processor is further configured to receive one or more electrode configurations.

13. The signal generator of claim 12, wherein the one or more electrode configurations are:
   received from a programmer module and based on the first tumor profile and a desired effect on the tumor, or
   obtained using a computer-implemented algorithm.

14. The signal generator of claim 13, wherein the one or more electrode configurations comprise an array of the plurality of electrodes on an implantation lead.

15. The signal generator of claim 14, wherein the one or more electrode configurations are selected from readily available implantation leads based on the profile and a desired effect on the tumor.

16. The signal generator of claim 14, wherein the implantation lead is configured for:
   implantation in a brain of a patient, or
   epidural implantation.

17. The signal generator of claim 13, wherein the one or more electrode configurations are customized based on the profile and a desired effect on the tumor.

18. The signal generator of claim 12, wherein an electrode configuration includes two or more electrodes and each of the two or more electrodes is stimulated with a different one or more of the one or more stimulation settings.

19. A signal generator coupled to a plurality of electrodes, the signal generator comprising:
   a processor configured to receive:
      a set of tumor-specific electromagnetic field data and generate a corresponding set of stimulation settings, wherein the set of stimulation settings comprise a specific output setting for each of the plurality of electrodes; and one or more electrode configurations comprising a configuration of the plurality of electrodes on an implantation lead,
wherein the implantation lead is integrated with a venous filter, and
wherein the configuration is based on a tumor profile or a computer-implemented algorithm and selected based on the profile and a desired effect on the tumor;
a memory configured to receive and store the set of stimulation settings from the processor; and
a communication engine configured to deliver the specific output settings to each corresponding one of the plurality of electrodes to generate a tumor-specific electromagnetic field based upon to the tumor-specific electromagnetic field data,
wherein the specific output settings include a set of electrical parameters based upon the tumor-specific electromagnetic field data.

* * * * *